(12) United States Patent
Silk et al.

(10) Patent No.: US 7,022,727 B2
(45) Date of Patent: Apr. 4, 2006

(54) CRYSTALLINE DRUG FORM

(75) Inventors: Terence Vernon Silk, Sandwich (GB); Julian Duncan Smith, Sandwich (GB)

(73) Assignee: Pfizer Inc, New York, NY (US)

( * ) Notice: Subject to any disclaimer, the term of this patent is extended or adjusted under 35 U.S.C. 154(b) by 15 days.

(21) Appl. No.: 10/934,903

(22) Filed: Sep. 3, 2004

(65) Prior Publication Data

US 2005/0085437 A1   Apr. 21, 2005

Related U.S. Application Data

(62) Division of application No. 10/308,805, filed on Dec. 3, 2002, now Pat. No. 6,852,746.

(60) Provisional application No. 60/352,424, filed on Jan. 28, 2002.

(30) Foreign Application Priority Data

Dec. 6, 2001  (GB) .................................. 0129273

(51) Int. Cl.
*A61K 31/70*   (2006.01)
*C07H 19/00*   (2006.01)

(52) U.S. Cl. ..................... 514/381; 514/45; 536/27.22; 536/26.13; 536/27.3; 536/27.62; 536/26.6; 536/22.1; 252/299.63; 546/296; 548/311.1

(58) Field of Classification Search ................ 514/381, 514/45; 536/27.22, 26.13, 27.3, 27.62, 22.1, 536/26.6; 252/299.63; 546/296; 548/311.1
See application file for complete search history.

(56) References Cited

U.S. PATENT DOCUMENTS 5,593,975 A   1/1997   Cristalli ....................... 514/46

FOREIGN PATENT DOCUMENTS

| WO | WO 9111172 | 8/1991 |
| WO | WO 9402518 | 2/1994 |
| WO | WO 9855148 | 12/1998 |
| WO | WO 0077018 | 12/2000 |
| WO | WO 0194368 | 12/2001 |
| WO | WO 0296462 | 5/2002 |
| WO | WO 0209462 | 12/2002 |

*Primary Examiner*—James O. Wilson
*Assistant Examiner*—Devesh Khare
(74) *Attorney, Agent, or Firm*—Gregg C. Benson; William F. Mulholland, II

(57) ABSTRACT

The present invention relates to a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide and to a process for the preparation of, compositions containing and the uses of such a crystalline form.

16 Claims, 3 Drawing Sheets

CRYSTALLINE DRUG FORM

CROSS REFERENCE TO RELATED APPLICATIONS

This application is a division of U.S. application Ser. No. 10/308,805, filed Dec. 3, 2002, now U.S. Pat. No. 6,852, 746B2 which claims the benefit of U.S. Provisional Application No. 60/352,424, filed Jan. 28, 2002, and United Kingdom Application Number 0129273.9, filed Dec. 6, 2001.

The present invention relates to a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide and to a process for the preparation of, compositions containing and the uses of such a crystalline form.

6-[(2,2-Diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide (also known as 6-[(2,2-diphenylethyl)amino]-9-{(2R,3R,4S,5S)-5-[(ethylamino)carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide) has the structure shown in formula (I) and its preparation is disclosed in International Patent Application number PCT/IB01/00973, published as WO-A-01/94368.

As described in PCT/IB01/00973, 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide is a selective, functional agonist of the human adenosine A2a receptor and may be used as an anti-inflammatory agent in the treatment of, inter alia, diseases of the respiratory tract. It may therefore be used to treat any disease for which an adenosine A2a receptor agonist is indicated. It can be used to treat a disease where leukocyte (e.g. neutrophil, eosinophil, basophil, lymphocyte, macrophage)-induced tissue damage is implicated. It is useful as an anti-inflammatory agent in the treatment of diseases of the respiratory tract such as adult respiratory distress syndrome (ARDS), bronchitis, chronic bronchitis, chronic obstructive pulmonary disease, cystic fibrosis, asthma, emphysema, bronchiectasis, chronic sinusitis and rhinitis. It may also be used in the treatment of septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastro-intestinal tract or a psychotic disorder, or for wound healing.

Examples 8 and 35 of PCT/IB01/00973 both describe the preparation of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide. These methods provide a solid, amorphous form of the compound (see comparative examples 1 and 2 below).

Before a drug compound can be commercialised, a process for its bulk manufacture must be developed that reliably provides a uniform and highly pure grade of the compound. Further, the process must deliver a form of the compound that can be suitably formulated for convenient dosage to patients and which is chemically and physically stable over long periods in that formulation.

A crystalline form of a drug compound has advantages over an amorphous form in several respects. For example, the compound can be easily purified by crystallisation and recrystallisation. Crystallisation is a much cheaper and more convenient method of purification to perform on a large scale than other known methods of purification such as chromatography. Further, a crystalline form is usually more stable than an amorphous form, both before and during formulation and during subsequent storage. Further, when formulating a drug for delivery by inhalation, it is generally easier to mill or micronise a crystalline form to a respirable size (generally considered as particles less than 5 microns in diameter) than an amorphous form.

There is no generally applicable method for preparing a crystalline form of an amorphous material. Indeed, it is impossible to know, from the outset, whether any crystalline form of a given compound exists. Where it turns out that a compound can be crystallised, extensive experimentation is usually required before a process is identified from which the crystalline form can be isolated. The correct combination of several independently variable conditions (for example, solvent concentration, solvent composition, temperature, cooling rate) must be identified empirically through trial and error with no guarantee of success.

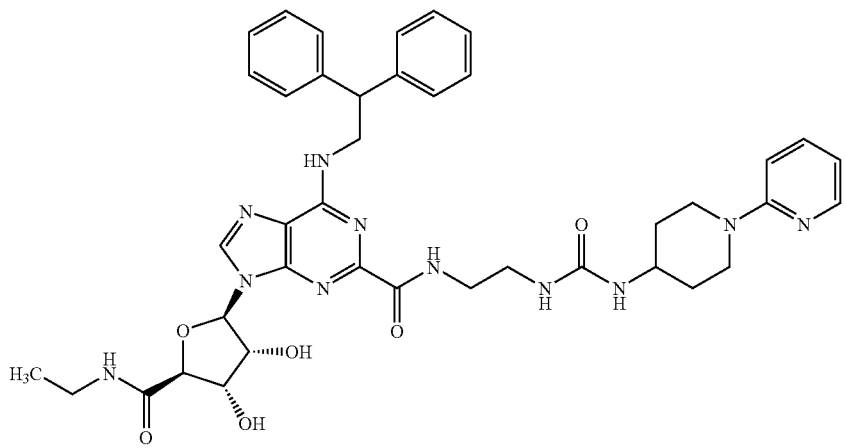

(I)

Many efforts to crystallise 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide were unsuccessful. Slurrying the compound in a range of solvents (e.g. methanol, ethanol, tetrahydrofuran, acetonitrile, dichloromethane, toluene) at ambient temperature, with and without added water was fruitless. Similarly, heating such slurries to obtain a solution and allowing them to cool in a conventional fashion did not provide a satisfactory crystalline form.

It has now been surprisingly found that a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide exists and may be prepared using the processes outlined below.

BRIEF DESCRIPTION OF THE DRAWINGS

The nature and mode of the present invention will be more clearly understood from the following detailed description taken together with the accompanying drawings wherein.

Figure 1:
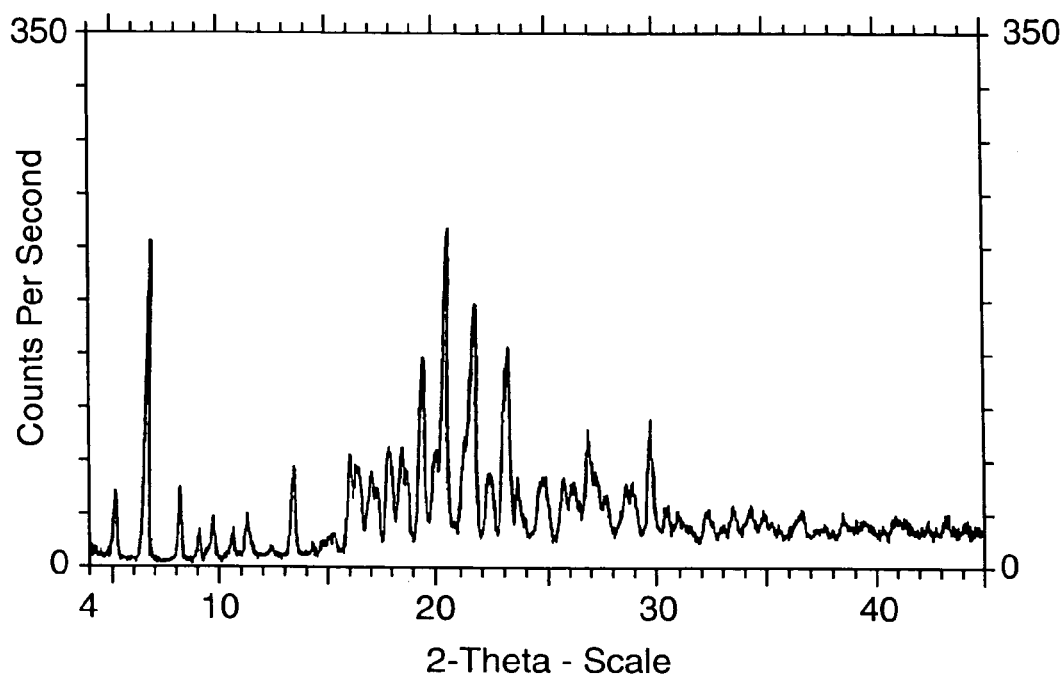
FIG. 1 illustrates the graphical results of an X-Ray diffraction pattern analysis performed on a compound obtained in accordance with the present invention.

The invention thus provides a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide.

The invention further provides a process for the preparation of a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide which comprises the steps of:

(a) dissolving amorphous 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide in an organic solvent which contains at least 2% w/w dissolved water; and (b) heating the solution so obtained to a temperature of at least 50° C. until crystallisation occurs.

This process is unusual in several respects. The solvent system developed (a solution of least 2% w/w water in an organic solvent) is not conventional. Further, crystallisation is initiated by maintaining the solution of amorphous compound in this solvent at an elevated temperature whereas in conventional crystallisation techniques, crystallisation is initiated by cooling such a solution. Thus, the process presented provides a unique and unconventional set of conditions that unexpectedly solve the problem of preparing a crystalline form of 6-[(2,2-diphenylethyl)amino]-9-(N-ethyl-β-D-ribofuranosyluronamide)-N-(2-{N'-[1-(2-pyridyl )-4-piperidyl]ureido}ethyl)-9H-purine-2-carboxamide.

The crystalline form provided by the above process has a further unexpected advantage in that it leads to a higher resistivity than the amorphous form at an equivalent concentration in solution. This is of particular benefit in preparing a formulation for use in an atomiser that operates by the principles of electrohydrodynamics (see below) since it is possible to lower the resistivity in such a formulation by the addition of, for example, sodium chloride, but it is currently not possible to raise it. Thus, the higher the resistivity of a compound when formulated in solution, the more flexibility exists in the choice of a final resistivity for the formulation.

Any organic solvent may be used in the process which is capable of dissolving both amorphous 6-[(2,2-diphenylethyl)amino]-9-(N-ethyl-β-D-ribofuranosyluronamide)-N-(2-{N'-[1-(2-pyridyl)-4-piperidyl]ureido}ethyl )-9H-purine-2-carboxamide and at least 2% w/w water. Examples of such a suitable solvent include 2-butanone, ethyl acetate, acetonitrile, isopropyl acetate, isopropanol, methyl acetate, butan-2-ol and methyl acetate. Preferred organic solvents are 2-butanone, methyl acetate and ethyl acetate. Methyl acetate and ethyl acetate are particularly preferred.

The water content of an organic solvent may conveniently be measured using the Karl-Fischer method.

A temperature of at least 50° C. is necessary to induce crystallisation at a practicable rate. Preferably, a temperature of from 50° C. to 80° C. is used.

Crystallisation will usually be complete within 24 to 72 hours but longer and shorter periods are possible depending on the choice of organic solvent and temperature.

The crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide (henceforth referred to as the 'compound of the invention') can be administered alone but will generally be administered in admixture with a suitable pharmaceutical excipient, diluent or carrier selected with regard to the intended route of administration and standard pharmaceutical practice.

For example, it can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. It may also be administered as fast-dispersing or fast-dissolving dosage forms or in the form of a high energy dispersion or as coated particles. Suitable formulations may be in coated or uncoated form, as desired.

Such solid pharmaceutical compositions, for example tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, sodium stearyl fumarate, sodium lauryl sulphate, stearic acid, glyceryl behenate and talc may be included.

GENERAL EXAMPLE

A formulation of the tablet could typically contain from 0.01 mg to 500 mg of active compound whilst tablet fill weights may range from 50 mg to 1000 mg. An example of a formulation for a 10 mg tablet is illustrated below:

| Ingredient | % w/w |
|---|---|
| Compound of the invention | 10.000* |
| Lactose | 64.125 |
| Starch | 21.375 |
| Croscarmellose sodium | 3.000 |
| Magnesium Stearate | 1.500 |

*Quantity adjusted in accordance with drug activity.

The tablets can be manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or a high molecular weight polyethylene glycol. For aqueous suspensions and/or elixirs, the compound of the invention may be combined with various sweetening or flavouring agents, colouring matter or dyes, with emulsifying and/or suspending agents and with diluents such as water, ethanol, propylene glycol or glycerin, and combinations thereof.

The compound of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration, it is best used in the form of a sterile aqueous solution which may contain other substances, for example, a co-solvent and/or enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compound of the invention will usually be from 0.00001 to 100 mg/kg, preferably from 0.0001 to 100 mg/kg (in single or divided doses).

Thus tablets or capsules of the compound of the invention may contain from 0.01 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compound of invention can also be administered intranasally or by inhalation and is conveniently delivered in the form of a dry powder (either alone or as a mixture, for example a mixture with lactose) from a dry powder inhaler or an aerosol spray presentation from a pressurised container, pump, spray, atomiser (preferably an atomiser using electrohydrodynamics to produce a fine mist) or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide, a further perfluorinated hydrocarbon such as Perflubron (trade mark) or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol (optionally, aqueous ethanol) or a suitable agent for dispersing, solubilising or extending release and the propellant as the solvent, which may additionally contain a lubricant, e.g. sorbitan trioleate. Capsules, blisters and cartridges (made, for example, from gelatin or HPMC) for use in an inhaler or insufflator may be formulated to contain a powder mix of the compound of the invention, a suitable powder base such as lactose or starch and a performance modifier such as I-leucine, mannitol or magnesium stearate.

Prior to use in a dry powder formulation or suspension formulation for inhalation the compound of the invention will be reduced to a particle size suitable for delivery by inhalation (typically considered as less than 5 microns). Production of particles in a suitable size range could be achieved by the use of a range of destructive methods, for example spiral jet milling or fluid bed jet milling or by use of a range of constructive methods such as supercritical fluid crystallisation or spray drying.

A suitable solution formulation for use in an atomiser using electrohydrodynamics to produce a fine mist may contain from 1 µg to 10 mg of the compound of the invention per actuation and the actuation volume may vary from 1 to 100 µl. A typical formulation may comprise the compound of the invention, propylene glycol, sterile water, ethanol and sodium chloride. Alternative solvents may be used in place of propylene glycol, for example glycerol or polyethylene glycol. A specific example of a formulation for use in an atomiser using electrohydrodynamics is illustrated below:

| Ingredient | Quantity |
|---|---|
| Compound of the invention | 14.6 mg |
| Propylene glycol | 0.08 ml |
| Sterile water | 0.02 ml |
| Ethanol | to 1 ml |
| Sodium chloride | as required to adjust resistivity to 1100 Ohm-m |

Aerosol or dry powder formulations are preferably arranged so that each metered dose or "puff" contains from 1 to 4000 µg of the compound of the invention for delivery to the patient. The overall daily dose with an aerosol will be in the range of from 1 µg to 20 mg which may be administered in a single dose or, more usually, in divided doses throughout the day.

Alternatively, the compound of the invention can be administered in the form of a suppository or pessary, or it may be applied topically in the form of a lotion, solution, cream, ointment or dusting powder. The compound of the invention may also be dermally or transdermally administered, for example, by the use of a skin patch. It may also be administered by the pulmonary, vaginal or rectal routes.

For application topically to the skin, the compound of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can. be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compound of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

It is to be appreciated that all references herein to treatment include curative, palliative and prophylactic treatment.

The crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide provided by the present invention may optionally be formulated in combination with other pharmacologically active compounds. Preferred combinations for use in the treatment of obstructive airways and other inflammatory diseases include (a) a crystalline form of 6-[(2,2-diphenylethyl) amino]-9-(N-ethyl-β-D-ribofuranosyluronamide)-N-(2-{N'-[1-(2-pyridyl)-4-piperidyl]ureido}ethyl)-9H-purine-2-carboxamide and (b) a corticosteroid, an adrenergic β2 agonist or an anticholinergic compound. Examples of preferred adrenergic β2 agonists are salmeterol and formoterol. Examples of preferred anticholinergic compounds are tiotropium, ipratropium and oxitropium salts.

Thus the invention provides:

(i) a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide;

(ii) a process for the preparation of a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide;

(iii) a pharmaceutical composition including a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide together with a pharmaceutically acceptable excipient, diluent or carrier;

(iv) a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2carboxamide for use as a medicament;

(v) a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2carboxamide for use as a medicament having A2a receptor agonist activity;

(vi) a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2carboxamide for use as an anti-inflammatory agent;

(vii) a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2carboxamide for use as a medicament for the treatment of a respiratory disease;

(viii) a crystalline form as in (vii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(ix) a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2carboxamide for use as a medicament for the treatment of septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastro-intestinal tract or a psychotic disorder, or for wound healing;

(x) the use of a crystalline form of 6-[(2,2-diphenylethyl) amino]-9-(N-ethyl-β-D-ribofuranosyluronamide)-N-(2-{N'-[1-(2-pyridyl)-4-piperidyl]ureido}ethyl)-9H-purine-2carboxamide for the manufacture of a medicament having A2a receptor agonist activity;

(xi) the use of a crystalline form of 6-[(2,2-diphenylethyl) amino]-9-(N-ethyl-β-D-ribofuranosyluronamide)-N-(2-{N'-[1-(2-pyridyl)-4-piperidyl]ureido}ethyl)-9H-purine-2carboxamide for the manufacture of an anti-inflammatory agent;

(xii) the use of a crystalline form of 6-[(2,2-diphenylethyl) amino]-9-(N-ethyl-β-D-ribofuranosyluronamide)-N-(2-{N'-[1-(2-pyridyl)-4-piperidyl]ureido}ethyl)-9H-purine-2carboxamide for the manufacture of a medicament for the treatment of a respiratory disease;

(xiii) use as in (xii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(xiv) the use of a crystalline form of compound of 6-[(2,2-diphenylethyl)amino]-9-(N-ethyl-β-D-ribofuranosyluronamide)-N-(2-{N'[1-(2pyridyl)-4-piperidyl] ureido}ethyl)-9H-purine-2-carboxamide for the manufacture of a medicament for the treatment of septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastro-intestinal tract or a psychotic disorder, or for wound healing;

(xv) a method of treatment of a mammal, including a human being, with an A2a receptor agonist including treating said mammal with an effective amount of a crystalline form of 6-[(2,2-diphenylethyl)amino]-9-(N-ethyl-β-D-ribofuranosyluronamide)-N-(2-{N'-[1-(2-pyridyl)-4-piperidyl] ureido}ethyl)-9H-purine-2-carboxamide;

(xvi) a method of treatment of a mammal, including a human being, to treat an inflammatory disease including treating said mammal with an effective amount of a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide;

(xvii) a method of treatment of a mammal, including a human being, to treat a respiratory disease including treating said mammal with an effective amount of a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide;

(xviii) a method as in (xvii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis; and (xix) a method of treatment of a mammal, including a human being, to treat septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroid al anti-inflammatory drug-induced damage to the gastro-intestinal tract or a psychotic disorder, or for wound healing, including treating said mammal with an effective amount of a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide.

The following Examples illustrate the invention.

EXAMPLE 1

Amorphous 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide (5.0 g, 0.0064 moles) was charged to a vessel equipped with a Teflon(Trade Mark)-covered magnetic stirrer bar, a thermometer and a condenser. A solution of 2% v/v water in 2-butanone (50 ml) was then added, and the resultant mixture was heated to 69–71° C. with stirring under an atmosphere of nitrogen to give an initially clear solution. After 24 hours at this temperature, a mobile white suspension had formed. The temperature of the mixture was then reduced to 59–61° C. and stirring was continued for an additional 24 hours. The mixture was then cooled to ambient temperature over 30 minutes and was stirred at this temperature for 1 hour. The solid was then collected by filtration and the filter cake was washed with 2-butanone (50 ml). The solid was then dried at 50° C. under reduced pressure for 48 hours to give the title compound as colourless crystals (3.99 g) that contained approximately 1% by weight of 2-butanone by $^1$H-NMR. Prior to obtaining further characterisation data, the material so formed was dried further at 50° C. under reduced pressure for 5 days to give 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide that contained approximately 0.5% by weight of 2-butanone. Measurement of the water content of this material showed that it also contained 1.6% by weight of water. Further drying at elevated temperature further reduced the levels of 2-butanone present, thereby demonstrating that residual 2-butanone is probably not an intrinsic part of the crystal lattice but is trapped within the channels of the crystal lattice.

The crystalline form produced by the process described above has the following characteristics:

Low Resolution Mass Spectrometry

Positive atmospheric pressure chemical ionisation: m/z [MH$^+$]778.

Proton NMR Spectroscopy (300 MHz, d$_6$-DMSO, 30° C.) δ: 8.80 (0.8H, br t), 8.67 (0.2H, br s), 8.53 (0.2H, br s), 8.48 (0.8H, s), 8.28 (1H, br t), 8.10–8.02 (1.8H, m), 7.84 (0.2H, br s), 7.50–7.30 (5H, m), 7.26 (4H, t), 7.14 (2H, t), 6.75 (1H, d), 6.56 (1H, dd), 6.11–5.82 (3H, m), 5.65 (1H, m), 5.60–5.45 (1H, m), 4.80–4.50 ((2.4H, m), 4.40–3.95 (5.6H, m), 3.67–3.55 (1H, m), 3.40–3.10 (6H, m (partly obscured by water peak)), 3.00–2.65 (2H, m), 1.74 (2H, br d), 1.30–1.16 (2H, br q), 0.98 (3H, t).

Acquiring the $^1$H-NMR spectrum at 70° C. results in the disappearance of signals attributable to the observation of more than one conformer at 30° C.

Infra-Red Spectroscopy

The infrared spectrum was acquired using a Nicolet 360 Avatar FT-IR spectrometer fitted with a d-TGS detector and a single reflection diamond ATR accessory (Golden Gate™). The sample was prepared by placing ca. 0.5 mg of sample on the diamond ATR crystal and ensuring good crystal sample contact by applying pressure through an anvil with a built-in pressure control mechanism. The spectrum was recorded at 4 cm$^{-1}$ resolution using 32 background and 32 sample scans with a Happ Genzel apodisation function.

Major peaks were recorded at 3478, 3395, 3375, 3301, 3060, 3024, 2971, 2943, 1657, 1639, 1597, 1552, 1527, 1494, 1475, 1468, 1456, 1434, 1405, 1374, 1351, 1324, 1310, 1300, 1233, 1220, 1163, 1150, 1123, 1113, 1102, 1078, 1054, 1000, 976, 947, 932, 909, 864, 813, 777, 759, 734, 699, 683 and 667 cm$^{-1}$.

Powder X-Ray Diffraction (PXRD)

The powder X-ray diffraction pattern was determined using a SIEMENS D5000 powder X-ray diffractometer fitted with an automatic sample changer, a theta-theta goniometer, automatic beam divergence slits, a secondary monochromator and a scintillation counter. The sample was prepared for analysis by packing the powder on to a silicon wafer specimen mount. The specimen was rotated whilst being irradiated with copper K-alpha$_1$ X-rays (wavelength=1.5406 Angstroms) with the X-ray tube operated at 40 kV/40 mA. The analysis was performed with the goniometer running in step-scan mode set for a 5 second count per 0.02° step over a two theta range of 4° to 45°.

The diffraction pattern obtained is shown in FIG. 1

The peak intensities of greater than 5% are summarised in Table 1. In Table 1, "Angle 2-Theta" is related to the interplanar spacing of the crystal, and the intensity is given as a percentage of the greatest peak (I/I$_r$).

TABLE 1

| Angle 2-Theta ° | Intensity % | Angle 2-Theta ° | Intensity % | Angle 2-Theta ° | Intensity % | Angle 2-Theta ° | Intensity % |
|---|---|---|---|---|---|---|---|
| 5.185 | 22.9 | 17.099 | 27.4 | 24.861 | 29.5 | 33.177 | 13.8 |
| 6.647 | 96.0 | 17.369 | 23.8 | 24.966 | 29.5 | 33.596 | 18.3 |
| 8.232 | 23.7 | 17.908 | 35.6 | 25.795 | 26.9 | 34.484 | 18.2 |
| 9.131 | 11.3 | 18.517 | 35.8 | 26.214 | 24.4 | 35.048 | 16.2 |
| 9.794 | 15.4 | 18.753 | 29.0 | 26.570 | 21.4 | 35.399 | 13.7 |
| 10.702 | 10.1 | 19.414 | 62.3 | 26.949 | 40.8 | 35.704 | 14.2 |
| 11.370 | 16.1 | 20.079 | 35.3 | 27.054 | 38.5 | 36.797 | 17.1 |
| 12.495 | 6.3 | 20.418 | 100 | 27.308 | 28.3 | 37.819 | 15.4 |
| 13.494 | 30.1 | 21.357 | 38.0 | 27.776 | 21.2 | 38.667 | 16.6 |
| 14.393 | 7.8 | 21.696 | 77.7 | 28.718 | 25.1 | 39.568 | 12.8 |
| 14.536 | 6.8 | 22.455 | 28.3 | 28.991 | 24.4 | 40.463 | 12.9 |
| 14.899 | 8.1 | 23.187 | 65.2 | 29.854 | 43.7 | 40.929 | 17.6 |
| 15.148 | 10.1 | 23.697 | 27.0 | 30.581 | 16.7 | 41.473 | 16.2 |
| 15.369 | 9.9 | 24.030 | 15.0 | 31.142 | 15.6 | 42.455 | 14.5 |
| 16.111 | 33.5 | 24.755 | 28.5 | 32.517 | 17.2 | 43.347 | 14.5 |
| 16.439 | 30.2 | | | | | | |

As will be appreciated by the skilled crystallographer, the relative intensities of the various peaks within Table 1 may vary due to a number of factors such as for example orientation effects of crystals in the X-ray beam or the purity of the material being analysed or the degree of crystallinity of the sample. The peak positions may also shift for variations in sample height but the peak positions will remain substantially as defined in Table 1.

The skilled crystallographer will also appreciate that measurements using a different wavelength will result in different shifts according to the Bragg equation—$n\lambda=2d \sin \theta$.

Such further PXRD patterns generated by use of alternative wavelengths are considered to be alternative representations of the PXRD pattern of the crystalline material of the present invention and as such are within the scope of the present invention.

Differential Scanning Calorimetry (DSC)

Differential scanning calorimetry was performed using a Perkin Elmer DSC-7 instrument fitted with an automatic sample changer. Approximately 3 mg of the sample was accurately weighed into a 50 microlitre aluminium pan and crimp sealed with a perforated lid. The samples were heated at 20° C./minute over the range 40° C. to 250° C. with a nitrogen gas purge.

Figure 2:
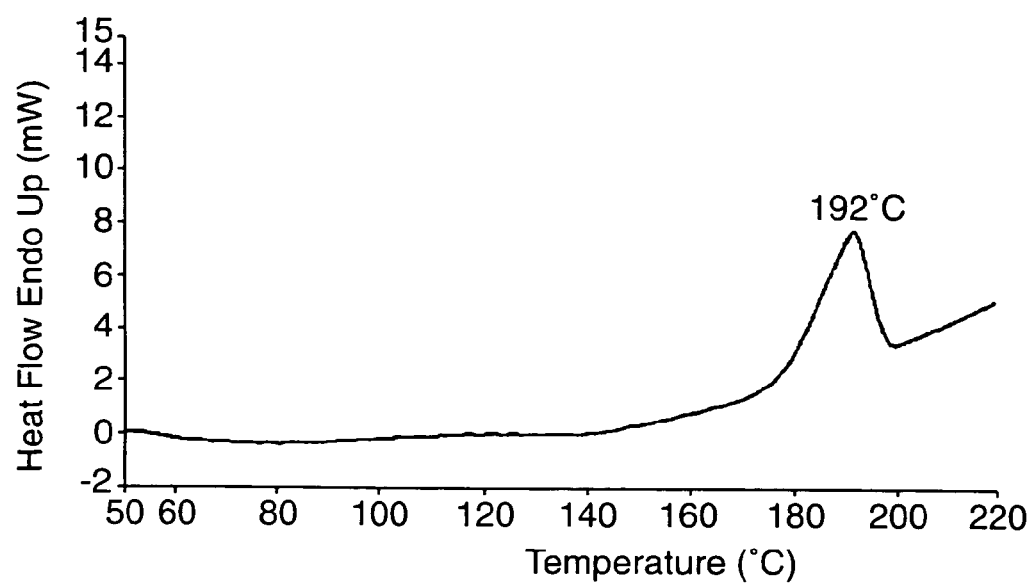
FIG. 2 illustrates the graphical results of a differential scanning calorimetry analysis performed on a compound obtained in accordance with the present invention.

The results are shown in FIG. 2. The melting range is approximately 185–195° C.

Thermal Gravimetric Analysis (TGA)

Thermal gravimetric analysis was performed using a Perkin Elmer Pyris1 TGA instrument fitted with an automatic sample changer. Approximately 8 mg of the sample was accurately weighed into a ceramic pan. The sample was heated at 20° C./minute over the range 25° C. to 350° C. with a nitrogen gas purge.

Figure 3:
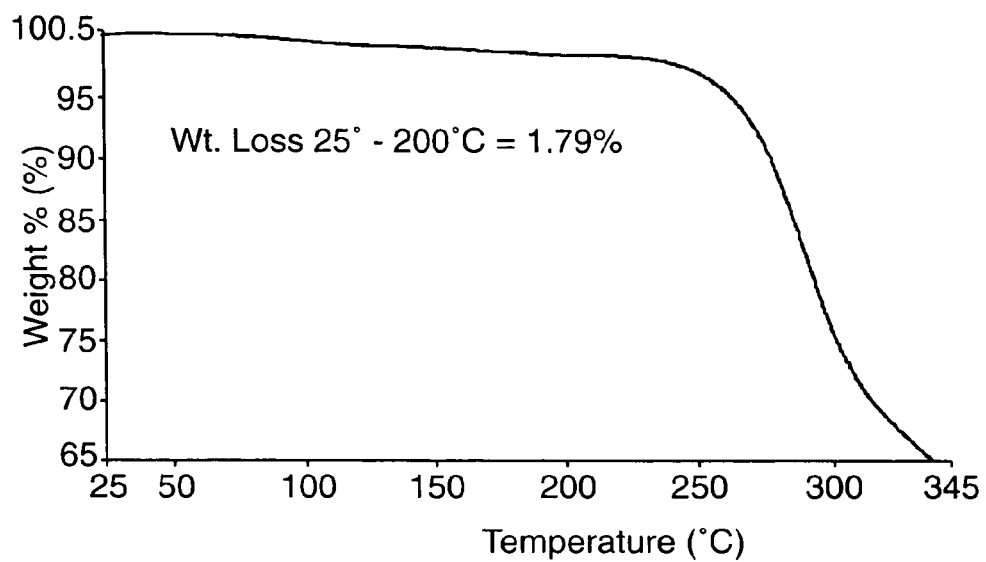
FIG. 3 illustrates the graphical results of a thermal gravimetric analysis performed on a compound obtained in accordance with the present invention.

The results are shown in FIG. 3.

EXAMPLE 2

To amorphous 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide (66.1 g, 0.085 moles) was added a 2% v/v solution of water in 2-butanone (660 ml) and the resultant mixture was heated at 69–71° C. for 18 hours. After this time, a seed of crystalline 6-[(2,2-diphenylethyl)amino]-9-(N-ethyl-β-D-ribofurano- syluronamide)-N-(2-{N'-[1-(2-pyridyl)-4-piperidyl] ureido}ethyl)-9H-purine-2-carboxamide (0.149 g) was added to the mixture and stirring at 69–71° C. was continued for 8 hours. The temperature of the mixture was then lowered to 59–61° C. and stirring at this temperature was continued for 64 hours. The resultant slurry was then cooled to ambient temperature and the solid was collected by filtration. The filter cake was washed with 2-butanone (2×100 ml) and the resultant solid was dried at 60° C. under vacuum for 60 hours, then at 80° C. under vacuum for 72 hours to give a crystalline solid (35.72 g) that contained traces of 2-butanone. Analytical data collected on the product, including characterisation by Powder X-Ray Diffraction, were consistent with the data described in Example 1.

EXAMPLE 3

Ethyl acetate (25 ml) was shaken with deionised water (10 ml) at ambient temperature and the organic phase was collected to give a solution of ethyl acetate that was saturated with water. Amorphous 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide (1.0 g, 0.0013 moles) was charged to a vessel equipped with a Teflon®-covered magnetic stirrer bar and a condenser. A solution of ethyl acetate that was saturated with water as prepared above (10 ml) was then added to the amorphous solid, and the resultant mixture was heated to 55–60° C. under an atmosphere of nitrogen. A seed (approximately 0.005 g) of crystalline 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide was then added and the resultant mixture was stirred at 55–60° C. for 3 days after which time a slurry had formed. The mixture was then cooled to ambient temperature and the solid was collected by filtration. The filter cake was then washed with ethyl acetate (2×5 ml) and the resultant solid was dried at 50° C. for 24 hours to give a crystalline solid (0.898 g) that contained traces of sodium chloride (inadvertently present in the starting material and subsequently filtered off with the product) and ethyl acetate. Analytical data collected on the product, including characterisation by Powder X-Ray Diffraction, were consistent with the data described in Example 1 except that a trace of sodium chloride was present.

EXAMPLE 4

A 2% v/v solution of water in acetonitrile was prepared by dissolving deionised water (2.0 ml) in acetonitrile and then making the volume up to 100 ml with acetonitrile. Amorphous 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide (1.0 g, 0.0013 moles) was charged to a vessel equipped with a teflon®-covered magnetic stirrer bar and a condenser. A 2% v/v solution of water in acetonitrile as prepared above (10 ml) was then added to the amorphous solid, and the resultant mixture was heated to 55–60° C. under an atmosphere of nitrogen. A seed (approximately 0.005 g) of crystalline 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide was then added and the resultant mixture was stirred at 55–60° C. for 3 days after which time a thick slurry had formed. The mixture was then cooled to ambient temperature and additional acetonitrile (10 ml) was added. The solid was then collected by filtration. The filter cake was then washed with acetonitrile (2×5 ml) and dried at 50° C. for 24 hours to give a crystalline solid (0.866 g) that contained traces of sodium chloride (inadvertently present in the starting material and subsequently filtered off with the product) and acetonitrile. Analytical data collected on the product, including characterisation by Powder X-Ray Diffraction, were consistent with the data described in Example 1 except that a trace of sodium chloride was present.

EXAMPLE 5

Isopropyl acetate (25 ml) was shaken with deionised water (10 ml) at ambient temperature and the organic phase was collected to give a solution of isopropyl acetate that was saturated with water. Amorphous 6-[(2,2-diphenylethyl)amino]-9-(N-ethyl-β-D-ribofuranosyluronamide)-N-(2-{N'-[1-(2-pyridyl)4-piperidyl]ureido}ethyl)-9H-purine-2-carboxamide (1.0 g, 0.0013 moles) was charged to a vessel equipped with a teflon®-covered magnetic stirrer bar and a condenser. A solution of isopropyl acetate that was saturated with water as prepared above (10 ml) was then added to the amorphous solid, and the resultant mixture was heated to 55–60° C. under an atmosphere of nitrogen. A seed (approximately 0.005 g) of crystalline 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide was then added and the resultant mixture was stirred at 55–60° C. for 3 days after which time a slurry had formed. The mixture was then cooled to ambient temperature and the solid was collected by filtration. The filter cake was then washed with isopropyl acetate (2×5 ml) and dried at 50° C. for 24 hours to give a colourless crystalline solid (0.445 g) that contained traces of sodium chloride (inadvertently present in the starting material and subsequently filtered off with the product) and isopropyl acetate. Analytical data collected on the product, including characterisation by Powder X-Ray Diffraction, were consistent with the data described in Example 1, except that a trace of sodium chloride was present.

EXAMPLE 6

A 2% v/v solution of water in isopropanol was prepared by dissolving deionised water (2.0 ml) in isopropanol and then making the volume up to 100 ml with isopropanol. Amorphous 6-[(2,2-diphenylethyl)amino]-9-(N-ethyl-β-D-ribofuranosyluronamide)-N-(2-{N'-[1-(2-pyridyl)4-piperidyl]ureido}ethyl)-9H-purine-2-carboxamide (1.0 g, 0.0013 moles) was charged to a vessel equipped with a teflon®-covered magnetic stirrer bar and a condenser. A 2% v/v solution of water in isopropanol as prepared above (10 ml) was then added to the amorphous solid, and the resultant mixture was heated to 55–60° C. under an atmosphere of nitrogen. A seed (approximately 0.005 g) of crystalline 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide was then added and the resultant mixture was stirred at 55–60° C. for 8 days over which time a slurry formed. The mixture was then cooled to ambient temperature and the solid was then collected by filtration. The filter cake was then washed with isopropanol (2×5 ml) and dried at 50° C. for 24 hours to give a colourless crystalline solid (0.866 g) that contained traces of sodium chloride (inadvertently present in the starting material and subsequently filtered off with the product) and isopropanol. Analytical data collected on the product, including characterisation by Powder X-Ray Diffraction, were consistent with the data described in Example 1 except that a trace of sodium chloride was present.

EXAMPLE 7

Amorphous 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide (1.0 g, 0.0013 moles) was charged to a vessel equipped with a teflon®-covered magnetic stirrer bar and a condenser. To this amorphous solid was then added methyl acetate (10 ml) and deionised water (0.20 ml), and the resultant mixture was heated to 55–60° C. under an atmosphere of nitrogen. A seed (approximately 0.005 g) of crystalline 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide was then added and the resultant mixture was stirred at 55–60° C. for 24 hours over which time a slurry formed. The mixture was then cooled to ambient temperature and the solid was then collected by filtration. The filter cake was then washed with methyl acetate (2×5 ml) and dried at 50° C. for 24 hours to give a colourless crystalline solid (0.860 g) that contained traces of sodium chloride (inadvertently present in the starting material and subsequently filtered off with the product) and methyl acetate. Analytical data collected on the product, including characterisation by Powder X-Ray Diffraction, were consistent with the data described in Example 1 except that a trace of sodium chloride was present.

EXAMPLE 8

Amorphous 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide (1.0 g, 0.0013 moles) was charged to a vessel equipped with a teflon®-covered magnetic stirrer bar and a condenser. To this amorphous solid was then added butan-2-ol (10 ml) and deionised water (0.20 ml), and the resultant mixture was heated to 55–60° C. under an atmosphere of nitrogen. A seed (approximately 0.005 g) of crystalline 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide was then added and the resultant mixture was stirred at 55–60° C. for approximately 3 weeks over which time a slurry slowly formed. The mixture was then cooled to ambient temperature and the solid was then collected by filtration. The filter cake was then washed with butan-2-ol (2×5 ml) and dried at 50° C. for several days to give a colourless crystalline solid (0.860 g) that contained traces of sodium chloride (inadvertently present in the starting material and subsequently filtered off with the product). Analytical data collected on the product, including characterisation by Powder X-Ray Diffraction, were consistent with the data described in Example 1 except that a trace of sodium chloride was present.

EXAMPLE 9

To a stirred suspension of 6-[(2,2-diphenylethyl)amino]-9-(N-ethyl-2,3-O-isopropylidene-β-D-ribofuranosyluronamide)-N-(2-{N'-[1-(2-pyridyl)-4-piperidyl]ureido}ethyl)-9H-purine-2-carboxamide (200 g, 0.245 moles) (see WO-A-01/94368) in deionised water (1000ml) was added methanesulfonic acid (17.5 ml, 0.269 moles) under an atmosphere of nitrogen. The resultant mixture was then heated at temperatures up to 95° C. and was stirred within this temperature range for approximately 5 hours during which time all the starting material was consumed. The reaction was then stopped by the addition of a 10% w/w aqueous solution of disodium hydrogen phosphate heptahydrate (82 ml) and the resultant solution was then cooled to ambient temperature after which time methyl acetate (2000 ml) was added. To the resultant mixture was then slowly added a 10% w/w aqueous solution of disodium hydrogen phosphate heptahydrate (1300 ml) with vigorous stirring. The phases were then allowed to separate, and the organic phase was washed with a 2% w/w aqueous solution of disodium hydrogen phosphate heptahydrate (2000 ml). After allowing the phases to separate, the organic layer was collected and additional methyl acetate (1000 ml) was added. The resultant mixture was then azeotropically dried by distillation at atmospheric pressure until the amount of water left in the mixture was approximately 2% w/w by Karl-Fischer analysis. This required the addition of more methyl acetate (3000 ml, added in portions over the duration of the distillation), and a total of approximately 3000 ml of distillate was collected. This gave a water level of 1.8% w/w in the mixture, which was then heated at reflux for 18 hours. Deionised water (4 ml) was then added to adjust the water content of the mixture to 2.0% w/w and reflux was continued for an additional 24 hours after which time a slurry had formed. The mixture was then cooled to ambient temperature and the solid was collected by filtration. The filter cake was washed with a 2% w/w solution of water in methyl acetate (200 ml then 400 ml), and dried at 50° C. under reduced pressure for 20 hours to give a crystalline material (155.6 g) that was contaminated with traces of inorganic salts. A suspension of this material (153.6 g) in a mixture of ethyl acetate (1070 ml) and ethanol (460 ml) was heated to reflux for 10 minutes to give a slightly cloudy solution. After cooling to ambient temperature, the mixture was filtered to give a clear filtrate which was then distilled at atmospheric pressure. During the course of the distillation additional ethyl acetate (2900 ml) was added in portions and a total of 2900 ml of distillate was collected. Towards the end of the distillation, it was necessary to a deionised water (60 ml, added in 2 portions) in order to keep the product in solution and to create the conditions necessary for crystallisation to occur. At the end point of the distillation, there was approximately 2 mol % of ethanol remaining and approximately 2.3% w/w of water present in the mixture. For convenience, the mixture was held at this point at ambient temperature for 60 hours. The mixture was then heated at approximately 60° C. for 30 hours during which time a slurry was formed. The mixture was then cooled to ambient temperature and the solid was collected by filtration. The filter cake was then washed with a 2% v/v solution of water in ethyl acetate (150 ml then 300 ml), and dried in vacuo at 70° C. to give a colourless crystalline solid (134 g) that contained traces of residual ethyl acetate. Analytical data collected on the product, including characterisation by Powder X-Ray Diffraction, were consistent with that described in Example 1.

COMPARATIVE EXAMPLE 1

Figure 4:
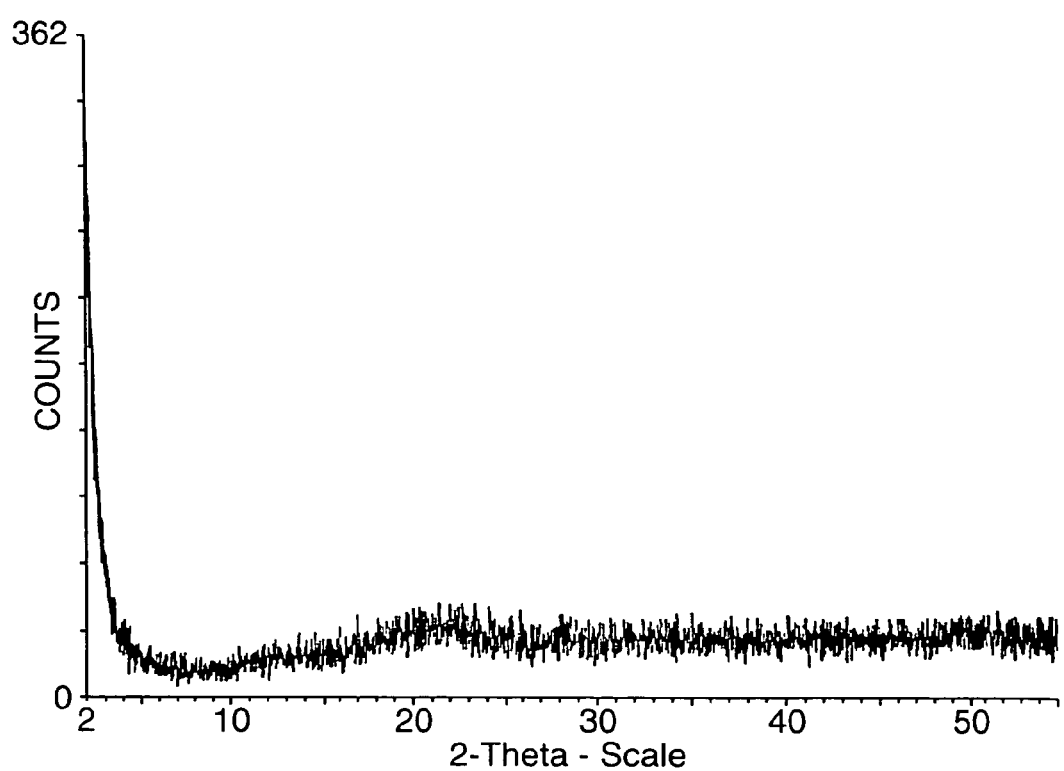
FIG. 4 illustrates the graphical results of an X-Ray diffraction pattern analysis performed on a sample of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide that had been prepared using the process described in Example 8 of WO-A-01/94368.

A sample of 6-[(2,2-diphenylethyl)amino]-9-(N-ethyl-β-D-ribofuranosyluronamide)-N-(2-{N'-[1-(2-pyridyl)-4-piperidyl]ureido}ethyl )-9H-purine-2-carboxamide that had been prepared using the process described in Example 8 of WO-A-01/94368 was examined by Powder X-Ray Diffraction, and was found to be non-crystalline. The respective X-ray diffraction pattern is shown in FIG. 4. The powder X-ray diffraction pattern was determined using a SIEMENS D5000 powder X-ray diffractometer fitted with an automatic sample changer, a theta-theta goniometer, automatic beam divergence slits, a secondary monochromator and a scintillation counter. The sample was prepared for analysis by packing the powder on to a silicon wafer specimen mount. The specimen was rotated whilst being irradiated with copper K-alpha$_1$ X-rays (wavelength=1.5406 Angstroms) with the X-ray tube operated at 40 kV/40 mA. The analysis was performed with the goniometer running in step-scan mode set for a 5 second count per 0.02° step over a two theta range of 40° to 55°.

COMPARATIVE EXAMPLE 2

Figure 5:
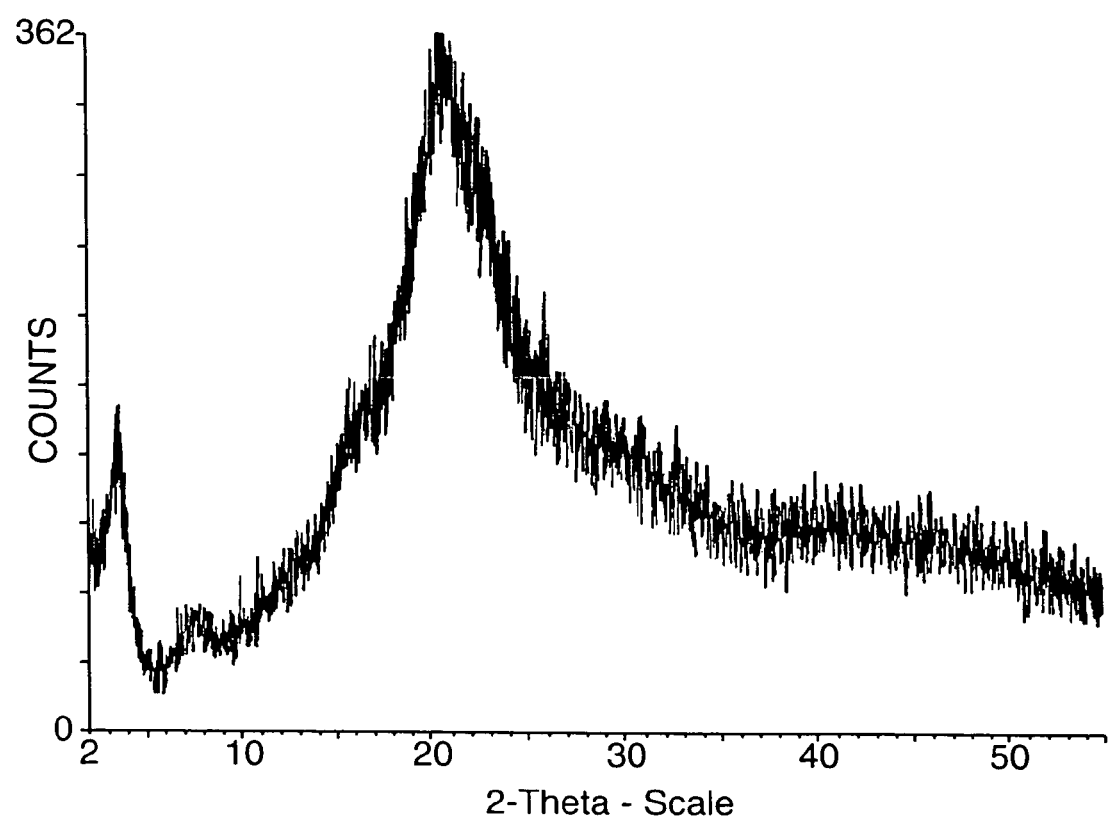
FIG. 5 illustrates the graphical results of an X-Ray diffraction pattern analysis performed on a sample of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide that had been prepared using the process described in Example 35 of WO-A-01/94368.

A sample of 6-[(2,2-diphenylethyl)amino]-9-(N-ethyl-β-D-ribofuranosyluronamide)-N-(2-{N'-[1-(2-pyridyl)4-piperidyl]ureido}ethyl)-9H-purine-2-carboxamide that had been prepared using the process described in Example 35 of WO-A-01/94368 was examined by Powder X-Ray Diffraction, and was found to be non-crystalline. The respective X-ray diffraction pattern is shown in FIG. 5. The powder X-ray diffraction pattern was determined using a SIEMENS D5000 powder X-ray diffractometer fitted with an automatic sample changer, a theta-theta goniometer, automatic beam divergence slits, a secondary monochromator and a scintillation counter. The sample was prepared for analysis by packing the powder on to a silicon wafer specimen mount. The specimen was rotated whilst being irradiated with copper K-alpha$_1$ X-rays (wavelength=1.5406 Angstroms) with the X-ray tube operated at 40 kV/40 mA. The analysis was performed with the goniometer running in step-scan mode set for a 5 second count per 0.02° step over a two theta range of 40° to 55°.

The invention claimed is:

1. A method of agonising an A2a receptor in a mammal comprising administering to said mammal in need thereof an effective amount of a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide.

2. The method of claim 1 wherein said crystalline form comprises a solid state infra-red spectrum which shows significant absorption bands at ν=3478, 3395, 3375, 3301, 3060, 3024, 2971, 2943, 1657, 1639, 1597, 1552, 1527, 1494, 1475, 1468, 1456, 1434, 1405, 1374, 1351, 1324, 1310, 1300, 1233, 1220, 1163, 1150, 1123, 1113, 1102, 1078, 1054, 1000, 976, 947, 932, 909, 864, 813, 777, 759, 734, 699, 683 and 667 cm$^{-1}$ and a powder X-ray diffraction pattern, obtained using copper K-alpha$_1$ X-rays (wavelength=1.5406 Angstroms), showing main peaks at 5.185, 6.647, 8.232, 9.131, 9.794, 10.702, 11.370, 12.495, 13.494, 14.393, 14.536, 14.899, 15.148, 15.369, 16.111, 16.439, 17.099, 17.369, 17.908, 18.517, 18.753, 19.414, 20.079, 20.418, 21.357, 21.696, 22.455, 23.187, 23.697, 24.030, 24.755, 24.861, 24.966, 25.795, 26.214, 26.570, 26.949, 27.054, 27.308, 27.776, 28.718, 28.991, 29.854, 30.581, 31.142, 32.517, 33.177, 33.596, 34.484, 35.048, 35.399, 35.704, 36.797, 37.819, 38.667, 39.568, 40.463, 40.929, 41.473, 42.455 and 43.347 degrees 2θ.

3. A method of treating an inflammatory disease in a mammal comprising administering to said mammal in need of such treatment an effective amount of a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide.

4. The method of claim 3 wherein said crystalline form comprises a solid state infra-red spectrum which shows significant absorption bands at ν=3478, 3395, 3375, 3301, 3060, 3024, 2971, 2943, 1657, 1639, 1597, 1552, 1527, 1494, 1475, 1468, 1456, 1434, 1405, 1374, 1351, 1324, 1310, 1300, 1233, 1220, 1163, 1150, 1123, 1113, 1102, 1078, 1054, 1000, 976, 947, 932, 909, 864, 813, 777, 759, 734, 699, 683 and 667 cm$^{-1}$ and a powder X-ray diffraction pattern, obtained using copper K-alpha$_1$ X-rays (wavelength=1.5406 Angstroms), showing main peaks at 5.185, 6.647, 8.232, 9.131, 9.794, 10.702, 11.370, 12.495, 13.494, 14.393, 14.536, 14.899, 15.148, 15.369, 16.111, 16.439, 17.099, 17.369, 17.908, 18.517, 18.753, 19.414, 20.079, 20.418, 21.357, 21.696, 22.455, 23.187, 23.697, 24.030, 24.755, 24.861, 24.966, 25.795, 26.214, 26.570, 26.949, 27.054, 27.308, 27.776, 28.718, 28.991, 29.854, 30.581, 31.142, 32.517, 33.177, 33.596, 34.484, 35.048, 35.399, 35.704, 36.797, 37.819, 38.667, 39.568, 40.463, 40.929, 41.473, 42.455 and 43.347 degrees 2θ.

5. A method of treating a respiratory disease in a mammal comprising administering to said mammal in need of such treatment an effective amount of a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide.

6. The method of claim 5 wherein said crystalline form comprises a solid state infra-red spectrum which shows significant absorption bands at ν=3478, 3395, 3375, 3301, 3060, 3024, 2971, 2943, 1657, 1639, 1597, 1552, 1527, 1494, 1475, 1468, 1456, 1434, 1405, 1374, 1351, 1324, 1310, 1300, 1233, 1220, 1163, 1150, 1123, 1113, 1102, 1078, 1054, 1000, 976, 947, 932, 909, 864, 813, 777, 759, 734, 699, 683 and 667 cm$^{-1}$ and a powder X-ray diffraction pattern, obtained using copper K-alpha$_1$ X-rays (wavelength=1.5406 Angstroms), showing main peaks at 5.185, 6.647, 8.232, 9.131, 9.794, 10.702, 11.370, 12.495, 13.494, 14.393, 14.536, 14.899, 15.148, 15.369, 16.111, 16.439, 17.099, 17.369, 17.908, 18.517, 18.753, 19.414, 20.079, 20.418, 21.357, 21.696, 22.455, 23.187, 23.697, 24.030, 24.755, 24.861, 24.966, 25.795, 26.214, 26.570, 26.949, 27.054, 27.308, 27.776, 28.718, 28.991, 29.854, 30.581, 31.142, 32.517, 33.177, 33.596, 34.484, 35.048, 35.399, 35.704, 36.797, 37.819, 38.667, 39.568, 40.463, 40.929, 41.473, 42.455 and 43.347 degrees 2θ.

7. The method of claim 5 wherein said disease is adult respiratory distress syndrome (ARDS), bronchitis, chronic bronchitis, chronic obstructive pulmonary disease (COPD), cystic fibrosis, asthma, emphysema, bronchiectasis, chronic sinusitis or rhinitis.

8. The method of claim 6 wherein said disease is adult respiratory distress syndrome (ARDS), bronchitis, chronic bronchitis, chronic obstructive pulmonary disease (COPD), cystic fibrosis, asthma, emphysema, bronchiectasis, chronic sinusitis or rhinitis.

9. A method of treating septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastrointestinal tract or a psychotic disorder, or for wound healing in a mammal comprising administering to said mammal in need of such treatment an effective amount of a combination of a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide.

10. The method of claim 9 wherein said crystalline form comprises a solid state infra-red spectrum which shows significant absorption bands at ν=3478, 3395, 3375, 3301, 3060, 3024, 2971, 2943, 1657, 1639, 1597, 1552, 1527, 1494, 1475, 1468, 1456, 1434, 1405, 1374, 1351, 1324, 1310, 1300, 1233, 1220, 1163, 1150, 1123, 1113, 1102, 1078, 1054, 1000, 976, 947, 932, 909, 864, 813, 777, 759, 734, 699, 683 and 667 cm$^{-1}$ and a powder X-ray diffraction pattern, obtained using copper K-alpha$_1$ X-rays (wavelength =1.5406 Angstroms), showing main peaks at 5.185, 6.647, 8.232, 9.131, 9.794, 10.702, 11.370, 12.495, 13.494, 14.393, 14.536, 14.899, 15.148, 15.369, 16.111, 16.439, 17.099, 17.369, 17.908, 18.517, 18.753, 19.414, 20.079, 20.418, 21.357, 21.696, 22.455, 23.187, 23.697, 24.030, 24.755, 24.861, 24.966, 25.795, 26.214, 26.570, 26.949, 27.054, 27.308. 27.776, 28.718, 28.991, 29.854, 30.581, 31.142, 32.517, 33.177, 33.596, 34.484. 35.048, 35.399, 35.704, 36.797, 37.819, 38.667, 39.568, 40.463, 40.929, 41.473, 42.455 and 43.347 decrees 2θ.

11. A process for preparing a crystalline form of 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide, comprising the steps of:
(a) dissolving amorphous 6-[(2,2-diphenylethyl)amino]-9-(N-ethyl-β-D-ribofuranosyluronamide)-N-(2-{N'-[1-(2-pyridyl)-4-piperidyl]ureido}ethyl)-9H-purine-2-carboxamide in an organic solvent which contains at least 2% w/w dissolved water to obtain a solution; and
(b) heating the solution to a temperature of at least 50° C. until crystallisation occurs.

12. A process of claim 11 wherein the organic solvent is 2-butanone, ethyl acetate, acetonitrile, isopropyl acetate, isopropanol, methyl acetate, butan-2-ol or methyl acetate.

13. A process of claim 11 wherein the organic solvent is 2-butanone, methyl acetate or ethyl acetate.

14. A process of claim 13 wherein the water content of the organic solvent is 2% v/v.

15. A process of claim 13 wherein the solution is heated to from 50° C. to 80° C.

16. A process of claim 14 wherein the solution is heated to from 50° C. to 80° C.

* * * * *